United States Patent
Sacquard et al.

(10) Patent No.: US 9,279,772 B2
(45) Date of Patent: Mar. 8, 2016

(54) SOILING CHECK OF THE WINDOW OF A MEASURING APPARATUS

(71) Applicant: GIESECKE & DEVRIENT GMBH, Munich (DE)

(72) Inventors: David Sacquard, Munich (DE); Shanchuan Su, Neubiberg (DE)

(73) Assignee: Giesecke & Devrient GMBH, Munich (DE)

( * ) Notice: Subject to any disclaimer, the term of this patent is extended or adjusted under 35 U.S.C. 154(b) by 180 days.

(21) Appl. No.: 14/353,195

(22) PCT Filed: Oct. 17, 2012

(86) PCT No.: PCT/EP2012/004344
§ 371 (c)(1),
(2) Date: Apr. 21, 2014

(87) PCT Pub. No.: WO2013/056826
PCT Pub. Date: Apr. 25, 2013

(65) Prior Publication Data
US 2014/0246611 A1    Sep. 4, 2014

(30) Foreign Application Priority Data

Oct. 20, 2011 (DE) .......................... 10 2011 116 487

(51) Int. Cl.
*G01N 21/84* (2006.01)
*G01N 21/15* (2006.01)
(Continued)

(52) U.S. Cl.
CPC ................ *G01N 21/84* (2013.01); *G01N 21/15* (2013.01); *G01N 21/86* (2013.01); *G01N 21/94* (2013.01); *G01N 2021/157* (2013.01)

(58) Field of Classification Search
CPC ....... G01N 21/86; G01N 21/94; G01N 21/84; G01N 21/15; G01N 2021/157
USPC .................... 250/559.1; 356/237.1
See application file for complete search history.

(56) References Cited

U.S. PATENT DOCUMENTS 4,352,988 A * 10/1982 Ishida ...................... G07D 7/00
250/559.11
4,723,072 A * 2/1988 Naruse ..................... G07D 7/12
209/534

(Continued)

FOREIGN PATENT DOCUMENTS

DE   19901702 A1   7/2000
DE   10159234 A1   6/2003
(Continued)

OTHER PUBLICATIONS

International Search Report from corresponding PCT Application No. PCT/EP2012/004344, Feb. 13, 2013.
(Continued)

Primary Examiner — Seung C Sohn
(74) Attorney, Agent, or Firm — Workman Nydegger

(57) ABSTRACT

A method for checking the soiling of the windows of a measuring apparatus for checking sheet material, includes having at least two sensor rows oriented transversally to the transport direction of the sheet material. Each of the sensor rows detects the light emanating from the sheet material in a certain spectral channel. For checking the soiling of the window the sensor rows detect the light at several detection times at which no sheet material is present in the capture area of the sensor rows. At least two of the spectral channels are combined with each other and the temporal variation of the intensities of the combined spectral channel is evaluated for the purpose of the soiling check. A small temporal variation of the intensity of the combined spectral channel is employed as an indicator for the presence of a soiling of the window.

15 Claims, 3 Drawing Sheets

(51) Int. Cl.
*G01N 21/86* (2006.01)
*G01N 21/94* (2006.01)

(56) References Cited

U.S. PATENT DOCUMENTS

| | | | |
|---|---|---|---|
| 6,472,670 | B1 | 10/2002 | Philipp et al. |
| 6,797,974 | B2 | 9/2004 | Philipp et al. |
| 8,107,712 | B2 * | 1/2012 | Holl ................ G07D 7/121 356/71 |
| 8,421,046 | B2 * | 4/2013 | Leuthold ............. G01N 21/15 134/37 |
| 2002/0092800 | A1 | 7/2002 | Philipp et al. |
| 2008/0243411 | A1 | 10/2008 | Pritzke et al. |

FOREIGN PATENT DOCUMENTS

| | | |
|---|---|---|
| DE | 10234431 A1 | 2/2004 |
| DE | 102004039049 A1 | 2/2006 |
| DE | 10 2007 014 844 B3 | 6/2008 |
| EP | 1 128 337 A1 | 8/2001 |
| WO | 00/42578 A1 | 7/2000 |

OTHER PUBLICATIONS

International Preliminary Report on Patentability from corresponding PCT Application No. PCT/EP2012/004344, Apr. 22, 2014.
German Search Report from German Application No. DE 10 2011 116 487.5, Jul. 17, 2012.

* cited by examiner

SOILING CHECK OF THE WINDOW OF A MEASURING APPARATUS

BACKGROUND

The present invention relates to a method for checking the soiling of a window of a measuring apparatus for checking sheet material, a measuring apparatus for carrying out the method and an apparatus for processing sheet material having the measuring apparatus.

SUMMARY

In apparatus for checking sheet material the sheet material is usually transported past a measuring apparatus along a transport direction and is illuminated on one or both surfaces so as to detect by means of a measuring apparatus the light remitted by the sheet material and/or the light transmitted by the sheet material. Between the transported sheet material and the measuring apparatus a window is arranged which is transmissive to the wavelengths to be detected, and which prevents mechanical damage or a soiling of sensitive components of the measuring apparatus. However, such windows are soiled in the course of time, so that the intensity of the light emanating from the sheet material that is detected by a measuring apparatus is distorted by the window soiling. This can lead to a wrong judgment of the sheet material upon the optical checking thereof. For example a soiling of the window along the transport direction of the sheet material can lead to stripes on an image detected of the sheet material. The window is therefore usually cleaned when a certain degree of soiling is reached.

To determine when a cleaning of the window of the measuring apparatus is required, the soiling of the window is regularly checked automatically. For this purpose the measuring apparatus detects the light impinging on the measuring apparatus when no sheet material is disposed in the capture area of the measuring apparatus. The detected intensity is compared e.g. with a reference value for a clean window. When the difference exceeds a predetermined value the necessity of cleaning is displayed or cleaning is carried out automatically. Alternatively, the window of the measuring apparatus can be cleaned manually. Since for cleaning usually the operation of the sheet material check must be interrupted, frequent cleaning works lead to a reduction of the throughput of the apparatus employed for checking the sheet material.

For checking the soiling of the window of the measuring apparatus so far the intensity of the background transversally to the transport direction of the sheet material is recorded when there is no sheet material present in the capture area of the measuring apparatus. Without sheet material present in the capture area the measuring apparatus usually detects only a low intensity. To check the window for soiling, the detected intensity of the background is compared to a threshold. When the intensity for one or several positions transversally to the transport direction exceeds the threshold, it is concluded that a soiling of the window is present in the concerned window section and cleaning of the window is initiated. However, it has turned out that despite this soiling check the checked sheet material is partly classified as faulty, e.g. soiled or defect, although the respective sheet material itself is not faulty.

The object of the present invention is consequently to achieve a more reliable soiling check of the window of a measuring apparatus.

This object is achieved by the subject matters of the independent claims. In claims dependent thereon advantageous developments and embodiments of the invention are specified.

It has turned out that the above-mentioned erroneous judgment of the sheet material results from the fact that the intensities detected upon checking the sheet material are distorted by a soiling of the window that is present despite the usual soiling check of the windows and has remained unrecognized so far. The invention is based on the finding that by the hitherto comparison of the detected intensity to a threshold only "light soiling" (predominantly light-scattering) is detectable. It was found that also a "dark soiling" (predominantly light-absorbing) occurs, which has been undetectable so far.

When no sheet material is present in the capture area of the measuring apparatus, and hardly any light impinges back on the measuring apparatus from the background of the sheet material to be detected, a low intensity is detected by the measuring apparatus in such positions transversal to the transport direction of the sheet material (hereinafter referred to as "y positions") which are disposed behind unsoiled window areas. Since in such y positions which are disposed behind a window area that is covered by dark soiling a low intensity is detected likewise, however, these cannot be distinguished on the basis of their intensity from such positions behind unsoiled window areas. The dark soiling has consequently remained unrecognized so far. Further also light soiling that scatters the light only slightly is not found reliably by the soiling check so far. When the window is clean the detected intensity varies as a function of the time, e.g. due to noise and/or disturbances from the surroundings. When a dark soiling is present, in contrast, a temporally relatively constant intensity is detected in such y positions in which the soiling is present. However, the time behavior of the intensity of one single spectral channel alone has turned out to be rather insignificant. Since disturbances or noise are in most cases present in several spectral channels, the detected intensities in the y positions without dark soiling vary in every single one of the several spectral channels. In the y positions with dark soiling, in contrast, a temporally relatively constant intensity is detected in several or all spectral channels.

The differences in the magnitude of the temporal variations are used for identifying dark soiling by a combination according to the invention of the spectral channels. By combining the spectral channels, the variations of several spectral channels have an effect on the combined spectral channel in the y positions in which the window does not have dark soiling. The combined spectral channel consequently has amplified intensity variations in the y positions without dark soiling, whereas in y positions with dark soiling only very small intensity variations occur.

The invention is characterized by the fact that at least two of the spectral channels are combined with each other and the temporal variation of the intensity of the combined spectral channel is evaluated for checking the soiling of the window of the measuring apparatus. A small temporal variation of the intensity of the combined spectral channel is employed as indicator for the presence of a dark soiling of the window in the respective y position.

The measuring apparatus has at least two sensor rows oriented transversally to the transport direction of the sheet material. Each of the sensor rows detects the light emanating from the sheet material in a certain spectral channel. The sensor rows each have several detection elements arranged side by side transversally to the transport direction of the sheet material. Each detection element forms e.g. one of several measuring tracks that are spaced apart from each other by gaps transversally to the transport direction. Alternatively, however, the sensor rows of the measuring apparatus can also be configured to record images of the sheet material and, through their detection elements, detect pixel by pixel, transversally to the transport direction of the sheet material, the intensity emanating from the illuminated sheet material. The soiling check can then be carried out on the basis of the images from the image sensor recorded in the different spectral channels. The sensor rows are e.g. CMOS, CCD or photodiode rows. The measuring apparatus can also have at least one light source for illuminating the sheet material. The illumination takes place in the visible spectral range, in the UV range or IR range. The light sources employed for illumination can form part of the measuring apparatus or can also be made available outside thereof. The intensities of the different spectral channels detected for the soiling check are preferably detected with the illumination turned on.

For checking the soiling of the window the sensor rows detect the light at several detection times at which no sheet material is present in the capture area of the sensor rows. In the evaluation carried out for the soiling check, the detected intensities of at least two of the sensor rows detecting spectral channels that differ from each other are evaluated, with each sensor row detecting the intensity transversally to the transport direction only in one certain spectral channel. The intensities are detected by the sensor rows for example in every y position for several detection times, in particular for at least 5 detection times, at which no sheet material is present in the capture area, e.g. several directly consecutive detection times. For each of the detection times the intensity of the combined spectral channel for the respective detection time is determined from the intensities detected by the sensor rows in their respective spectral channel at the detection time. Thus, for each of the detection times individually an intensity of the combined spectral channel is obtained as a function of the y position transversally to the transport direction of the sheet material. In at least one of the y positions transversally to the transport direction subsequently a statistical evaluation is carried out of the intensities of the combined spectral channel determined for the different detection times. The results of this temporal statistic are employed for checking the soiling of the window of the measuring apparatus.

Preferably the sensor rows detect the intensities in several y positions along the y direction in their respective spectral channel when no sheet material is present in the capture area of the sensor rows. The intensities are for example detected over one or several sections that are contiguous in the y direction. In an embodiment the intensities detected by the sensor rows of the different spectral channels at the respective detection time are combined for several of the y positions respectively individually to form an intensity of the combined spectral channel. The intensity detected in a spectral channel in a y position can be an intensity that was detected by a single detection element. Or the intensity detected in a y position in a spectral channel can be obtained by joining the intensities detected in this spectral channel by some detection elements that are adjacent transversally to the transport direction to form one resulting intensity of this spectral channel.

Preferably the statistical evaluation of the intensities of the combined spectral channel is carried out individually respectively for several of the y positions and it is checked on the basis of the statistical evaluation for several of the y positions whether or not a soiling of the window of the measuring apparatus is present in the respective y position of the window.

In particular, the statistical evaluation of the intensities of the combined spectral channel comprises the forming of a temporal standard deviation of the intensities of the combined spectral channel determined for the several detection times, particularly preferably also the forming of a temporal average value of the intensities of the combined spectral channel.

In the statistical evaluation for example a quotient is formed, containing in its numerator the temporal average value of the intensity of the combined spectral channel, and in its denominator the temporal standard deviation of the intensity of the combined spectral channel. The numerator and/or the denominator can contain a value determined from the average value or from the standard deviation, e.g. the denominator the square of the standard deviation. The numerator can contain an offset correction of the average value. Additionally, in the numerator and/or in the denominator of the quotient also further parameters and/or normalization factors can be contained. In particular, the temporal standard deviation of the intensities of the combined spectral channel is determined respectively individually for several of the y positions and is evaluated for the soiling check. In particular also the temporal average value and the above-mentioned quotient are formed respectively individually for several of the y positions.

For the soiling check of the window the quotient from the average value and the standard deviation can be compared to a threshold value, in particular individually for each of the y positions. The exceeding of the threshold value is employed as in indication that a soiling of the window could be present in the respective y position in which the threshold value is exceeded. It may be concluded that a soiling is actually present every time that a threshold value is exceeded, or only when the threshold value is exceeded in several, e.g. adjacent y positions. Alternatively or additionally to the threshold comparison the quotient of the average value and the standard deviation, in particular for several of the y positions respectively individually, can be compared to one or several of the quotients formed for y positions that are adjacent in the y direction, drawing a conclusion with regard to a soiling of the window on the basis of the differences between the quotients in the different y positions.

The intensity of the combined spectral channel can be determined by a mathematical concatenation of the intensities of the at least two different spectral channels. In particular, the combining by the mathematical concatenation can be carried out respectively individually for several of the y positions. The mathematical concatenation can be an addition, subtraction, division or multiplication of the intensities of the at least two spectral channels. Optionally, the individual spectral channels are incorporated in the intensities of the combined spectral channel with different weighting, in the case that the dark soilings have a differently strong effect on the different spectral channels. Which concatenation works most reliably is dependent on the respective cause giving rise to the variations of the detected intensities.

For determining the intensity of the combined spectral channel preferably a nonlinear transformation is carried out of the intensity of at least one of the at least two spectral channels to be combined with each other. Preferably the intensities of all spectral channels combined with each other are nonlinearly transformed before or upon the determination of the combined spectral channel. In particular, the nonlinear transformation can be carried out respectively individually for several of the y positions. The nonlinear transformation comprises e.g. exponentiating the intensity detected in the spectral channel and subsequently concatenating the exponentiated intensities of the individual spectral channels. The nonlinear transformation has the advantage that the variations of the detected intensities occurring in the non-soiled window areas are thus amplified, so that the distinction from the window areas with dark soiling is facilitated. To be able to carry out the nonlinear transformation of the detected intensities in real time, said transformation can be made available in the form of a look-up table stored in the evaluation device.

Preferably the method is carried out for two or more different combined spectral channels, with the results of the statistical evaluation of all of these combined spectral channels being employed and optionally mutually concatenated logically for the purpose of the soiling check of the window. Optionally, several combined spectral channels are formed and evaluated which employ different types of concatenation.

The measuring apparatus can be configured to measure the remission of the sheet material and of the light remitted by the window. Alternatively or additionally the measuring apparatus can be configured to measure the transmission of the sheet material and the light transmitted by the window. For checking the soiling of the window the remitted and/or the transmitted light is detected and evaluated by the measuring apparatus. Correspondingly, the light detected by the sensor rows is a light remitted by the window and/or a light transmitted by the window. The spectral channels employed for the checking the window soiling can be the same that are also employed for checking the sheet material. However, also different spectral channels can be employed for this purpose. For example the soiling check is carried out on the basis of light in the visible range and/or on the basis of light in the IR range and/or on the basis of light in the UV range.

For the soiling check of the window the sensor rows detect the intensity of the light impinging on the sensor rows at such times at which no sheet material is disposed in the capture area of the sensor rows. The soiling check is thus not carried out on the basis of the intensities detected from the sheet material, but exclusively on the basis of the intensities detected when no sheet material is present in the capture area of the sensor rows. Regarding the time sequence of the checking of sheet material and the soiling check of the windows it is possible to carry out the soiling check as an extra measurement in a singling break of the sheet-material processing machine or during the checking of the sheet material, in the gap between two sheets of the sheet material transported past the measuring apparatus.

Alternatively, the soiling check of the window is not carried out as an extra measurement at a time at which no sheet material is disposed in the capture area of the sensor row. Rather, for checking the sheet material an individual measurement of a sheet material can be carried out over a slightly longer period of time than would be required for recording an image of the sheet material at the respective transport speed. The recorded image consequently does not only contain the sheet material itself, but, viewed in the transport direction, also covers a slightly larger area, so that in the image also a section in front of and/or behind the sheet material is contained. This section of the recorded image can therefore be employed for the soiling check of the window of the measuring apparatus. For the soiling check of the window then a corresponding two-dimensional image area is evaluated, which is arranged next to the sheet material in the recorded image, i.e. which was recorded at a time before or after the sheet material. The length of the image area along the transport direction corresponds preferably to at least 5 detection times of the sensor rows. The advantage of this alternative is that singling breaks of the machine are omitted that had to be taken so far for the soiling measurement of the windows. Instead, the image area of an image recorded during the checking of the sheet material can be employed for checking the window soiling. Preferably, a corresponding image area is selected and evaluated for the window soiling check at regular intervals, i.e. after a predetermined number of sheet material transported past, for example for every hundredth image. It is also possible to carry out a joint evaluation of several images. To check a soiling of the window it is also possible to jointly evaluate corresponding image areas of several images.

The soiling check is preferably limited in a targeted fashion to one or several partial areas of the windows, namely such partial areas of the windows which actually play a role in the checking of the sheet material to be checked respectively. These are the window areas through which the light actually passes that emanates from the sheet material and is evaluated for the check of the sheet material. A soiling of a window that is located transversally to the transport direction outside of the relevant window area is not considered in the soiling check, and thus no cleaning action is initiated. Unnecessary cleaning actions due to a soiling in an area of a window that is outside of the partial area relevant for the check of the banknote are thus prevented. The above-mentioned image area therefore preferably represents the window area that, with regard to its width and position in the beam path of the light, corresponds to the checked area of the sheet material on the basis of which the sheet material is checked.

The invention also relates to the measuring apparatus configured to carry out the method according to the invention. For this purpose the measuring apparatus has e.g. an evaluation device with corresponding programming. The measuring apparatus can form part of an apparatus for checking sheet material in which the measuring apparatus is installed. In dependence on the result of the soiling check a cleaning of the window can be initiated automatically by the measuring apparatus. When a window soiling is found, the operation of the apparatus can be interrupted automatically and/or a message can be output that the window needs to be cleaned. With the interruption of operation also an automatic cleaning of the window can be triggered, for example by blown air. It can also be provided that this soiling must be detected upon several consecutive soiling checks for a cleaning of the window to be initiated.

The apparatus configured to check sheet material can be so configured that the sheet material is guided through the apparatus along a transport path. The apparatus in which the measuring apparatus is received can be an apparatus for checking value documents, in particular a banknote processing machine for checking banknotes, e.g. a sorting machine, a deposit machine or a dispensing machine. It is possible to check sheet material of any desired kind, in particular value documents, such as for example banknotes, checks, tickets, vouchers, etc.

BRIEF DESCRIPTION OF THE DRAWINGS

Hereinafter the invention will be explained by way of example with reference to the following figures. The figures are described as follows.

DETAILED DESCRIPTION OF VARIOUS EMBODIMENTS

Figure 1A:
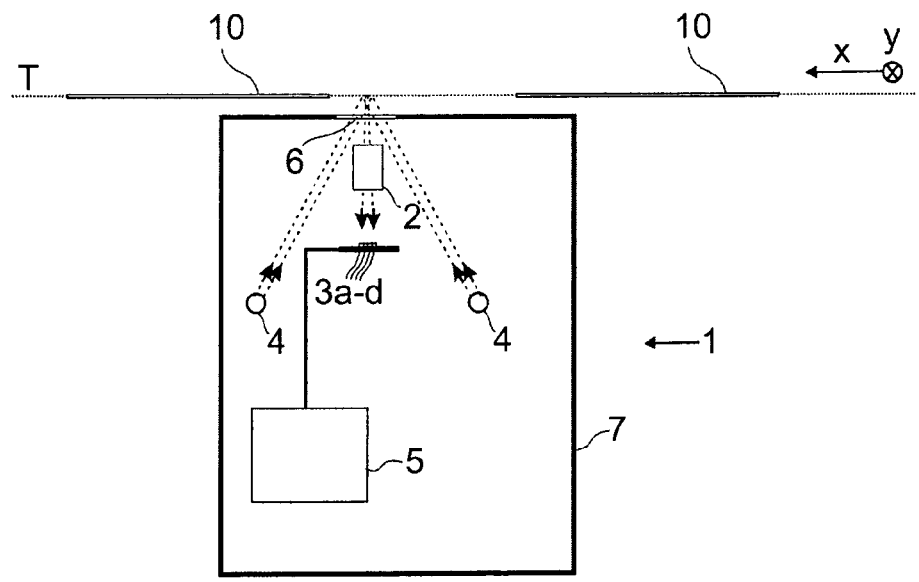
FIG. 1a-b schematic representations of a measuring apparatus according to the invention for carrying out the soiling check according to the invention, FIG. 2a-f intensity for two spectral channels detected at a certain time $t_1$ (FIG. 2a-b), intensity of a combined spectral channel determined on the basis thereof (FIG. 2c), average value (FIG. 2d) and standard deviation (FIG. 2e) of the intensities of the combined spectral channel and quotient formed therefrom (FIG. 2f), FIG. 3a-e intensities for three spectral channels detected at a certain time $t_1$ (FIG. 3a-c) and the quotient formed from the average value and the standard deviation of the intensities of the combined spectral channel (FIG. 3d-e) for two different combined spectral channels.

FIG. 1 shows a measuring apparatus for checking sheet material transported past the measuring apparatus on a transport path T along a transport direction x. The measuring apparatus 1 has a housing 7 in which two light sources 4 and four sensor rows 3a-d are received. Each of the sensor rows 3a-d is sensitive only to one certain spectral range and is equipped e.g. with a corresponding spectral filter for this purpose. By the light sources 4 light is irradiated through the window 6 onto the surface of a sheet material 10 present in the capture area of the measuring apparatus 1. The light is remitted by the surfaces of the sheet material, again passes the window 6 and, after passing suitable optical elements 2, e.g. lenses, is detected by the sensor rows 3a-d. The checking of the sheet material and of the soiling of the window in this example is carried out on the basis of a remission measurement, but can also be carried out on the basis of a transmission measurement, e.g. a dark-field transmission measurement. The measuring apparatus can also be arranged on both sides of the transport path T, with the sheet material e.g. being guided between two windows of the measuring apparatus behind which respective light sources and sensor rows are arranged. The soiling check can be carried out for both windows.

The measuring apparatus 1 in this example is an image sensor recording respectively line by line an image of the sheet material 10 transported past along the transport direction x. The sensor rows 3a-d of the measuring apparatus 1 detect the light e.g. in the 4 spectral channels red (R), green (G), blue (B) and infrared (IR). For the soiling check of the window 6 of the measuring apparatus 1 the intensities of the background are detected along a direction y transversal to the transport direction x of the sheet material 10, when no sheet material 10 is present in the capture area of the measuring apparatus 1. The light sources 4 remain e.g. permanently turned on during the checking of the sheet material and of the window soiling.

Figure 1B:
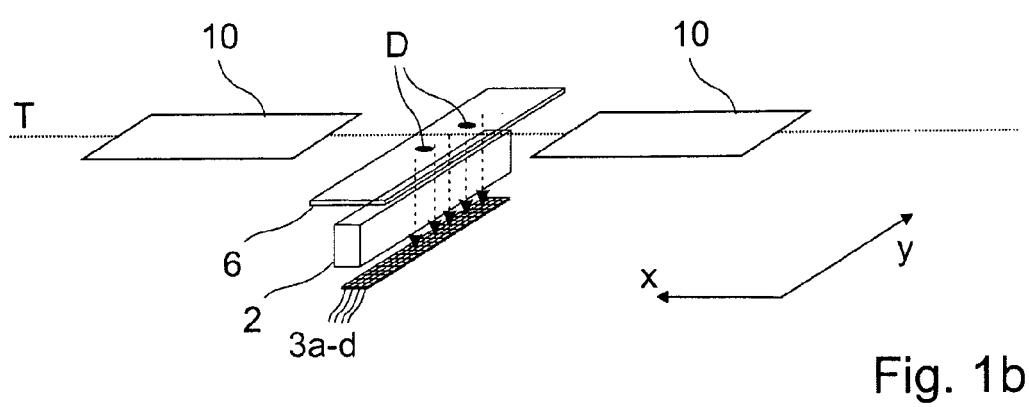

In FIG. 1b a detail of the arrangement of FIG. 1a is shown in a perspective view. On the window 6 a dark soiling D is drawn in two exemplary y positions along the y direction, whereas the other window areas are free of soiling. By means of the soiling check according to the invention it is found out which pixels of the sensor rows 3a-d, viewed along the detection ray beam, are arranged behind a dark soiling D, and a conclusion is drawn as to the presence of a dark soiling D in the corresponding y position of the window 6.

Figure 2:
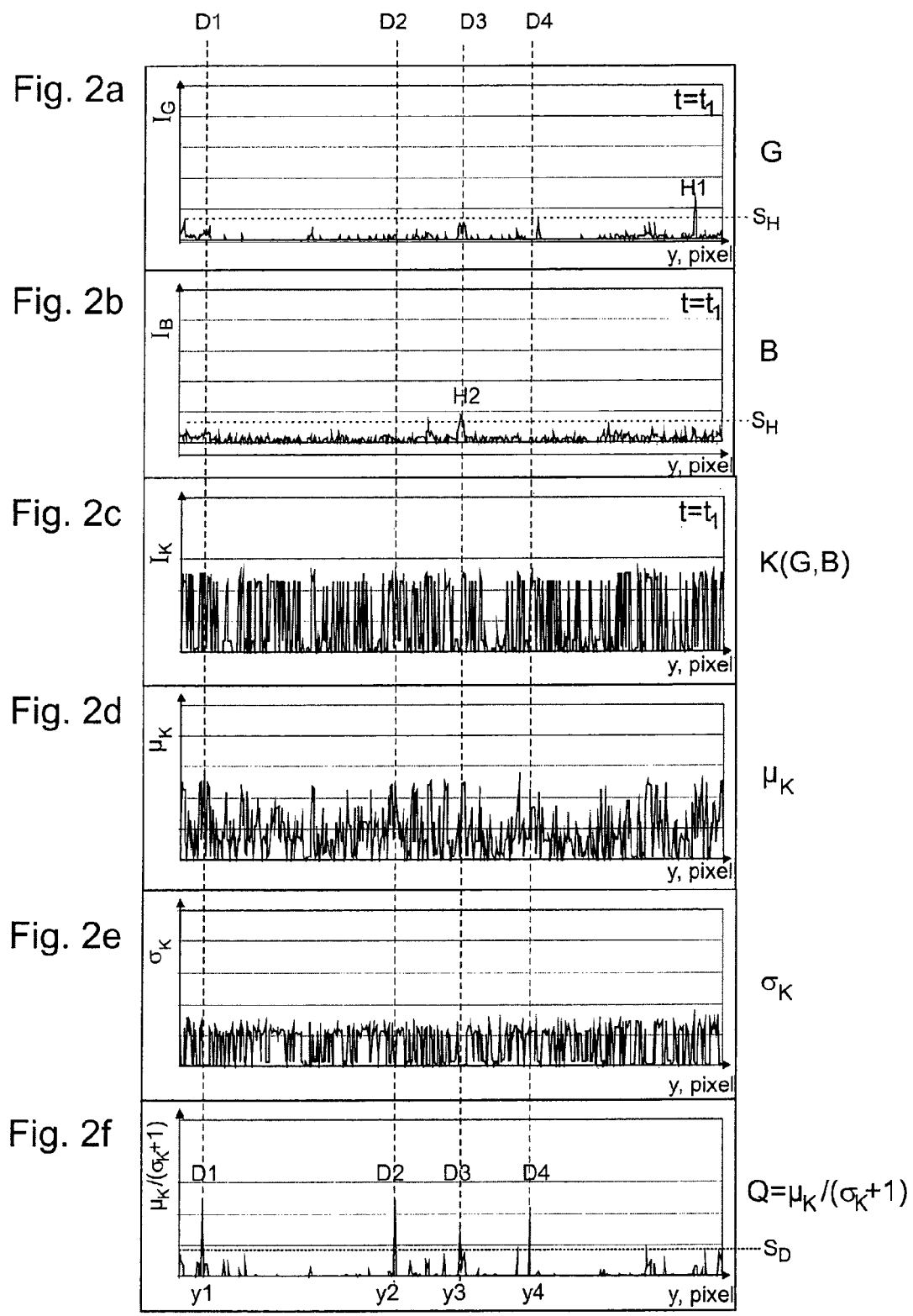

In the FIGS. 2a and 2b the intensities $I_G$ of the spectral channel G and $I_B$ of the spectral channel B are represented as a function of the y position (transversal to the transport direction), which are detected by two of the sensor rows 3a-d at a certain time $t_1$, at which no sheet material 10 is present in the capture area of the sensor rows 3a-d. Without sheet material present in the capture area, the sensor rows 3a-d detect only a relatively small intensity of the background in each pixel. To check the window for possibly soiled window areas, the thus detected background intensities $I_G$, $I_B$ are compared to a threshold $S_H$, cf. FIG. 2a, 2b. When the intensity $I_G$, $I_B$ exceeds the threshold $S_H$ for one or several pixels, it is concluded that a light soiling of the window is present in this section of the window disposed in front of this pixel. In this example a "light soiling" H1 is detected in the spectral channel G and a light soiling H2 is detected in the spectral channel B. Additionally, the window 6 is checked for dark soiling by means of the method according to the invention. The soiling check is carried out by an evaluation device 5 of the measuring apparatus, which can be arranged inside or outside of the housing 7 of the measuring apparatus.

The intensities $I_G$ and $I_B$ are detected at several consecutive times $t=t_1, t_2, t_3, \ldots$, at which no sheet material is present in the capture area. For each of these times $t=t_1, t_2, t_3, \ldots$ the intensity of a combined spectral channel K is determined individually. FIG. 2c shows the intensity $I_K$ of the combined spectral channel K valid for the time $t_1$, which is determined pixel by pixel from the intensities $I_G$ and $I_B$ of the FIGS. 2a and 2b. To combine the spectral channels G and B in this example the intensities $I_G$ and $I_B$ are each transformed nonlinearly, to obtain a nonlinear amplification of the variations of the intensities $I_G$, $I_B$ of the respective spectral channel G, B. As nonlinear transformation it is possible to employ e.g. a power function $a_G \cdot I_G^r$, $a_B \cdot I_B^r$, with the exponent r, wherein $r<1$ or $r>1$, and the weighting factors $a_G$ and $a_B$. The nonlinearly transformed intensities are concatenated with each other subsequently, e.g. subtracted from each other or added to each other.

From the intensities $I_K$ of the combined spectral channel K determined for the different times $t=t_1, t_2, t_3, \ldots$ there is subsequently determined, for each y position individually, their (temporal) average value $\mu_K$ and their (temporal) standard deviation $\sigma_K$. These are applied as a function of the y position in FIG. 2d, 2e. The average value $\mu_K(y)$ results from a temporal averaging over the intensities $I_K(y, t)$ of the combined spectral channel K, which is determined as a function of the time t, for different locations y along the y direction (along the window 6 transversally to the transport direction).

From the average value $\mu_K$ and the standard deviation $\sigma_K$ subsequently the quotient $Q=\mu_K/(1+\sigma_K)$ is formed, which is applied in FIG. 2f individually for each of the y positions. For the soiling check the quotient Q is compared e.g. to a threshold $S_D$, cf. FIG. 2f. In those y positions in which the threshold $S_D$ is exceeded, it is concluded that a dark soiling D of the window 6 of the measuring apparatus 1 is present. In the shown example the quotient Q exceeds the threshold $S_D$ in the four y positions y1, y2, y3, y4, in which consequently dark soilings D1, D2, D3, D4 are found. In these positions y1, y2, y3, y4 a very small standard deviation $\sigma_K$ is found, cf. FIG. 2e, and simultaneously an average value $\mu_K$ that substantially exceeds the lowest average values present along the y direction, cf. FIG. 2d.

In the positions y1, y2, y4 of the dark soilings D1, D2, D4 no intensities $I_G$ and $I_B$ that exceed the threshold $S_H$ are detected in the spectral channels G and B themselves, cf. FIGS. 2a and 2b. Thus soilings are found in the form of D1, D2, D4 which are not found by the hitherto check for light soiling. In the position y3 the dark soiling D3 is found, which also leads to a slightly increased signal also in the detected intensities $I_G$, $I_B$ themselves, cf. FIGS. 2a, 2b. However, in the y position y3 the threshold $S_H$ of the light soiling check is exceeded exclusively in the spectral channel B, and only slightly. By the soiling check according to the invention a soiling such as the one in the y position y3 can be found substantially more reliably. Preferably for the soiling check of the window 6 both the hitherto soiling check (cf. FIGS. 2a-b) to check for light soiling and the soiling check according to the invention (cf. FIGS. 2c-f) for dark soiling are employed to reliably find both types of soiling.

Figure 3:
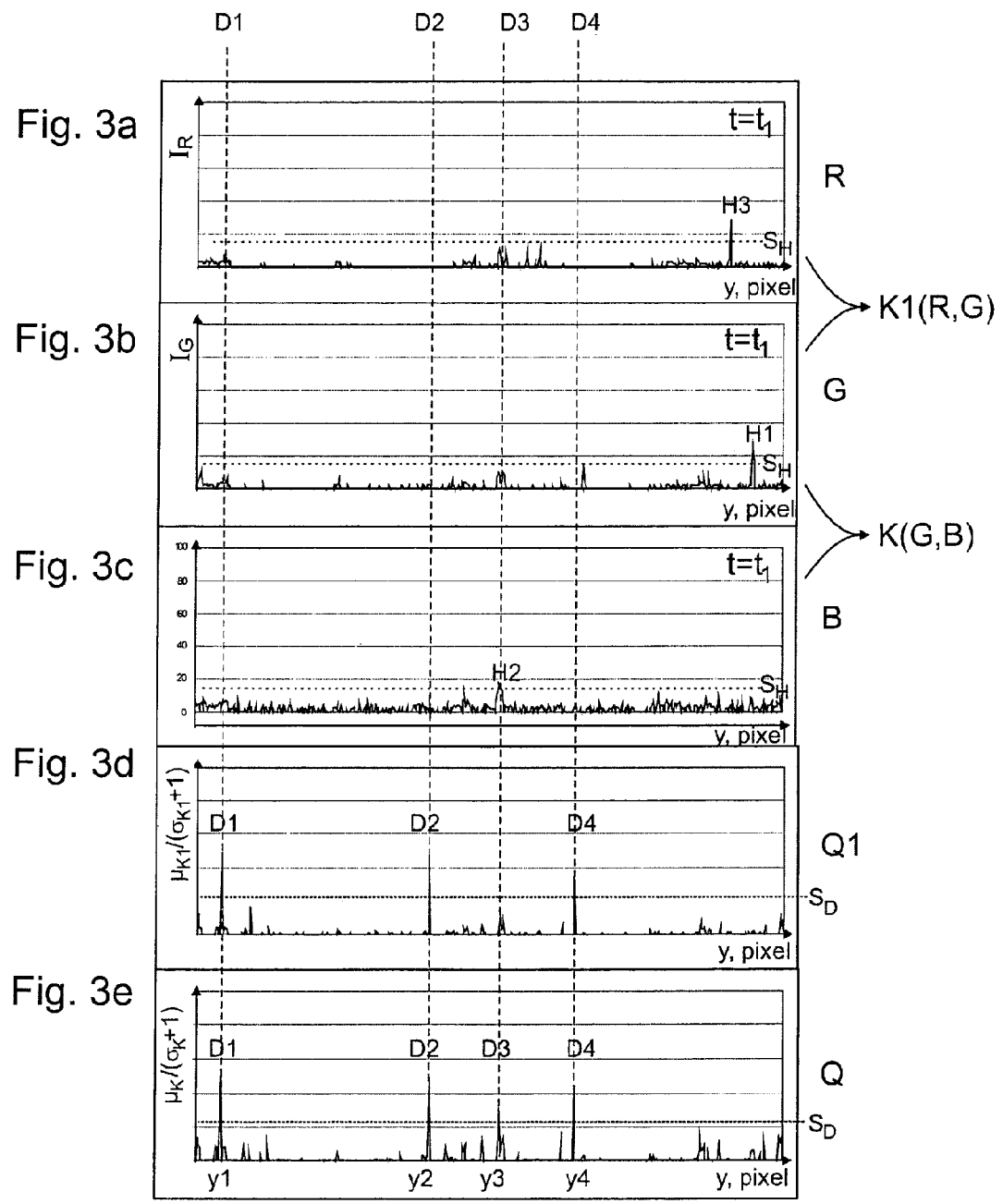

In FIGS. 3b and 3c the intensities $I_G$ and $I_B$ of the FIGS. 2a and 2b are applied for comparison to the intensity $I_R$ of the red spectral channel R detected at the time $t_1$, cf. FIG. 3a. In the spectral channel R a further light soiling H3 is found. Further, in FIG. 3e the curve already shown in FIG. 2f of the quotient $Q=\mu_K/(1+\sigma_K)$ is applied as a function of the y position that was determined for the combined spectral channel K. For comparison thereto in FIG. 3d the quotient $Q1=\mu_{K1}/(1+\sigma_{K1})$ for a further combined spectral channel K1 is shown, which results from combining the spectral channel R with the spectral channel G. The further combined spectral channel K1 is determined by a nonlinear transformation of the intensities $I_R$ and $I_G$ of the spectral channels R and G and a concatenation of the nonlinearly transformed intensities analogously to the spectral channel K, wherein merely the spectral channel R is employed instead of the spectral channel G, and the spectral channel G is employed instead of the spectral channel B. With the aid of an analogous threshold comparison the dark soilings D1, D2 and D4 can also be found by means of the quotient Q1, cf. FIG. 3d. However, it can also be provided that in the evaluation it is concluded that a dark soiling is present only provided that an exceeding of the respective threshold is ascertained in the same y position in two or more combined channels. These thresholds can be at the same or different levels.

The invention claimed is:

1. A method for checking the soiling of a window of a measuring apparatus for checking sheet material that is transported past the measuring apparatus along a transport path in a transport direction, wherein the measuring apparatus
   has respectively one sensor row for at least two different spectral channels, said sensor row having several detection elements along a y-direction transversal to the transport direction of the sheet material, to detect light emanating from a sheet material, when a sheet material is present in the capture area of the sensor row, and
   has at least one window arranged between the sensor rows and the transport path of the sheet material; and
   wherein for checking the soiling of the window the intensities of the light impinging on the sensor rows through the window are detected when no sheet material is present in the capture area of the sensor rows;
   wherein for checking the soiling of the window at least two of the sensor rows with different spectral channel detect respectively at least in one y-position along the y-direction the intensity of the light impinging on the respective sensor row through the window respectively for several detection times, when no sheet material is present in the capture area of the sensor rows, and
   from the intensities detected by the at least two sensor rows with different spectral channel at a detection time, an intensity of a combined spectral channel is determined, wherein the intensity of the combined spectral channel is determined individually for respectively several of the detection times, and
   a statistical evaluation is carried out for the intensities of the combined spectral channel determined for the several detection times, and
   on the basis of the statistical evaluation a soiling check of the window of the measuring apparatus is carried out.

2. The method according to claim 1, wherein when no sheet material is present in the capture area of the sensor rows, the sensor rows detect in their respective spectral channel the intensities in several y-positions along the y-direction, and that the intensities detected in the several y-positions are employed for checking the soiling of the window.

3. The method according to claim 2, wherein the intensities detected by the sensor rows of the different spectral channels at the respective detection time are combined for several of the y-positions respectively individually to form an intensity of the combined spectral channel.

4. The method according to claim 2, wherein the statistical evaluation of the intensities of the combined spectral channel is carried out respectively individually for several of the y-positions, and that it is checked respectively individually for several of the y-positions on the basis of the statistical evaluation whether a soiling of the window of the measuring apparatus is present in the respective y-position of the window.

5. The method according to claim 1, wherein the determining of the intensity of the combined spectral channel respectively individually for several of the y-positions comprises a nonlinear transformation of the intensity of at least one of the at least two spectral channels.

6. The method according to claim 1, wherein the statistical evaluation of the intensity of the combined spectral channel respectively individually for several of the y-positions comprises that the curve of the intensity of the combined spectral channel as a function of the time for at least 5 detection times is statistically evaluated in at least 5 consecutive detection times.

7. The method according to claim 1, wherein the statistical evaluation of the intensities of the combined spectral channel respectively individually for several of the y-positions, comprises the forming of a temporal standard deviation of the intensities of the combined spectral channel, which are determined for the several detection times, preferably the forming of a temporal average value and of a temporal standard deviation.

8. The method according to claim 7, wherein in the statistical evaluation respectively individually for several of the y-positions, a quotient is formed in whose numerator the temporal average value of the intensity of the combined spectral channel is contained, and in whose denominator the temporal standard deviation of the intensity of the combined spectral channel is contained.

9. The method according to claim 8, wherein for checking the soiling of the window the quotient of the average value and the standard deviation is compared to a threshold value respectively individually for several of the y-positions, and it is concluded upon exceeding the threshold value that a soiling of the window is present in the respective y-position in which the threshold value is exceeded.

10. The method according to claim 7, wherein the quotient of the average value and the standard deviation respectively individually for several of the y-positions, is compared to one or several of the quotients formed for one or several of the adjacent y-positions in the y-direction, and a conclusion is drawn as to a soiling of the window on the basis of the differences between the quotients in the different y-positions.

11. The method according to claim 1, wherein the method is carried out for at least two different combined spectral channels, wherein for checking the soiling of the window the results of the statistical evaluation of the at least two combined spectral channels are employed.

12. The method according to claim 1, wherein for checking the sheet material an image of the sheet material is detected which goes beyond the sheet material along the transport direction, and that for checking the soiling of the window an image area is evaluated that is arranged on the image in front of and/or behind the sheet material in the transport direction.

13. A measuring apparatus for checking sheet material transported past the measuring apparatus along a transport path in a transport direction, having:
   for at least two different spectral channels respectively one sensor row having several detection elements along a y-direction transversal to the transport direction of the sheet material, to detect light emanating from the sheet material when a sheet material is present in the capture area of the sensor rows, and, for checking the soiling of the window, to detect the intensities of the light impinging on the sensor rows through the window when no sheet material is present in the capture area of the sensor rows, at least one window arranged between the sensor rows and the transport path of the sheet material, and at least one evaluation device configured to evaluate the intensities of the light detected by the sensor rows for checking the soiling of the window, wherein the measuring apparatus is so configured that for checking the soiling of the window at least two of the sensor rows with different spectral channel detect, in at least one y-position along the y-direction, respectively the intensity of the light impinging on the sensor row through the window for several detection times, when no sheet material is present in the capture area of the sensor lines, and the evaluation device is configured to determine, from the intensities detected by the sensor rows with different spectral channel at a detection time, an intensity of a combined spectral channel, wherein an intensity of the combined spectral channel is determined respectively individually for several of the detection times, and to carry out a statistical evaluation of the intensities of the combined spectral channel determined for the several detection times and to carry out a soiling check of the window of the measuring apparatus on the basis of the results of the statistical evaluation.

14. The measuring apparatus according to claim 13, wherein the evaluation device is configured to carry out a method for checking the soiling of a window of the measuring apparatus for checking sheet material that is transported past the measuring apparatus along the transport path in the transport direction.

15. An apparatus for processing value documents, which is adapted to transport sheet material past a measuring apparatus along a transport path, wherein the measuring apparatus is a measuring apparatus according to claim 13.

* * * * *